United States Patent
Hald et al.

(10) Patent No.: US 9,276,297 B2
(45) Date of Patent: Mar. 1, 2016

(54) LITHIUM ION BATTERY CELL HAVING A CAPACITANCE SENSOR AND METHOD FOR MONITORING THE CONDITION OF A LITHIUM ION BATTERY CELL OF THIS TYPE

(71) Applicants: Robert Bosch GmbH, Stuttgart (DE); Samsung SDI Co., Ltd., Yongin-si, Gyeonggi-do (KR)

(72) Inventors: Markus Hald, Jagstzell (DE); Sarmimala Hore, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 97 days.

(21) Appl. No.: 14/296,556

(22) Filed: Jun. 5, 2014

(65) Prior Publication Data
US 2014/0363705 A1    Dec. 11, 2014

(30) Foreign Application Priority Data
Jun. 5, 2013    (DE) .................. 10 2013 210 378

(51) Int. Cl.
| | |
|---|---|
| H01M 10/48 | (2006.01) |
| G01N 27/22 | (2006.01) |
| H01M 10/0525 | (2010.01) |
| H01M 10/42 | (2006.01) |
| H01M 2/34 | (2006.01) |
| H01M 2/12 | (2006.01) |
| G01R 31/36 | (2006.01) |

(52) U.S. Cl.
CPC ............. *H01M 10/48* (2013.01); *G01N 27/221* (2013.01); *H01M 2/12* (2013.01); *H01M 2/345* (2013.01); *H01M 10/0525* (2013.01); *H01M 10/4264* (2013.01); *G01N 2027/222* (2013.01); *G01R 31/3606* (2013.01); *H01M 2010/4271* (2013.01); *H01M 2200/20* (2013.01); *H01M 2220/20* (2013.01); *Y02E 60/122* (2013.01)

(58) Field of Classification Search
None
See application file for complete search history.

(56) References Cited

U.S. PATENT DOCUMENTS

| | | | |
|---|---|---|---|
| 6,794,067 B1 * | 9/2004 | Acker ............... | H01M 8/04194 429/408 |
| 2008/0003473 A1 * | 1/2008 | Tung ................... | H01M 8/0215 429/435 |
| 2011/0183168 A1 * | 7/2011 | Johnnie ............... | H01M 10/484 429/93 |
| 2011/0217573 A1 | 9/2011 | Kritzer et al. | |

* cited by examiner

*Primary Examiner* — Patrick Ryan
*Assistant Examiner* — Wyatt McConnell
(74) *Attorney, Agent, or Firm* — Maginot, Moore & Beck LLP

(57) ABSTRACT

A lithium ion battery cell includes a graphite cathode, and an excess pressure valve. The excess pressure valve is configured to open in the presence of a predetermined battery cell internal pressure and discharging gases that have been produced inside the battery cell. Such gases are discharged together with graphite particles entrained in the gas. The battery cell further includes a capacitance sensor that has at least one capacitor positioned in the battery cell and configured such that the graphite particles that are entrained in the gas that is being discharged deposit themselves at least in part in a gap that is located between two electrodes of the capacitor and cause a change in the dielectric value in the gap. The change in the dielectric value causes a change in a capacitance of the capacitor.

10 Claims, 3 Drawing Sheets

LITHIUM ION BATTERY CELL HAVING A CAPACITANCE SENSOR AND METHOD FOR MONITORING THE CONDITION OF A LITHIUM ION BATTERY CELL OF THIS TYPE

This application claims priority under 35 U.S.C. §119 to patent application no. DE 10 2013 210 378.6, filed on Jun. 5, 2013 in Germany, the disclosure of which is incorporated herein by reference in its entirety.

The present disclosure relates to a lithium ion battery cell having a graphite cathode and an excess pressure valve that is provided for the purpose of opening in the presence of a predetermined battery cell internal pressure and discharging gases that have been produced inside the battery cell, said gases being discharged together with graphite particles that are entrained in the gas that is being discharged. Moreover, the disclosure relates to a method for monitoring the condition of a lithium ion battery cell of this type. The disclosure also relates to a battery system comprising a plurality of lithium ion battery cells of this type.

BACKGROUND

It is possible as a result of a defect for gas to be produced in lithium ion battery cells. As a consequence, an excess pressure arises inside the lithium ion battery cells. In the presence of a defined pressure inside a battery cell of this type, an excess pressure valve opens in order to discharge the gases and to avoid the battery cell becoming thermally unstable. During this process, graphite dust that is released from the graphite cathode of a battery cell of this type is also discharged and deposits itself on the surface of the battery cell.

It is known from the prior art to use capacitance sensors for many purposes such as by way of example for ascertaining spacings, pressures, fill levels or moisture contents. Capacitance sensors function on the basis of the change in the capacitance of an individual capacitor or of an entire capacitor system. The capacitance can be influenced in numerous ways that mostly arise as a result of the selected application.

SUMMARY

In accordance with the disclosure, a lithium ion battery cell having a graphite cathode and an excess pressure valve is provided. The excess pressure valve is provided for the purpose of opening in the presence of a predetermined battery cell internal pressure and discharging gases that have been produced inside the battery cell, said gases being discharged together with graphite particles that are entrained in any discharged gases. The battery cell comprises at least one capacitor that is embodied and arranged in the battery cell in such a manner that any entrained graphite particles are deposited at least in part in a gap that is located between the two electrodes of the capacitor and cause a change in the dielectric value in the gap that is located between the electrodes of the capacitor and said change causes a change in the capacitance of the capacitor.

Moreover, in accordance with the disclosure, a method is provided for monitoring the condition of a lithium ion battery cell having a graphite cathode and an excess pressure valve. The excess pressure valve is provided for the purpose of opening in the presence of a predetermined battery cell internal pressure and discharging gases that have been produced inside the battery cell, said gases being discharged together with graphite particles that are entrained in any discharged gases. A capacitance at least of one capacitor that is provided in the battery cell is measured during the course of the method. The capacitor is embodied and arranged in the battery cell in such a manner that any entrained graphite particles are deposited at least in part in a gap that is located between the two electrodes of the capacitor and said graphite particles cause a change in the dielectric value in the gap that is located between the electrodes of the capacitor. Moreover, in the presence of a change in the capacitance of the capacitor, said change being caused by a change in the dielectric value in the gap that is located between the two electrodes of the capacitor, it is established that the battery cell is defective in that gas is discharged from the battery cell through the open excess pressure valve.

The claims disclose further developments of the disclosure.

In the case of the present disclosure, the defect of a battery cell is established with the aid of a capacitance sensor. Subsequently, a defective battery cell of this type that is arranged in a battery system can be discharged by way of the battery management system of the battery system. This is not possible in the case of the battery systems that are known from the current prior art.

The graphite particles that are entrained in gases that are being discharged from a defective battery cell deposit themselves on a capacitor that is suitably provided in a battery cell in accordance with the disclosure. The capacitance of the capacitor changes as a consequence. This renders it possible to establish the defect of the battery cell.

In a preferred embodiment of the disclosure, the battery cell comprises a measuring circuit that is embodied for the purpose of measuring a capacitance of the capacitor and ascertaining a change in capacitance. The measuring circuit is preferably further embodied for the purpose of providing information regarding an ascertained change in the capacitance of the capacitor to a communication site that is provided in the battery cell for the purpose of communicating with a battery management system.

In a different very much preferred embodiment of the disclosure, the battery cell comprises an energy supply circuit that can be connected or is connected to the two electrodes of the capacitor and is embodied for the purpose of positively charging one of the two electrodes of the capacitor and negatively charging the other of the two electrodes of the capacitor.

It is preferred that the gap that is located between the electrodes of the capacitor is an open gap and/or an air gap.

In simple terms, the capacitor that is encompassed by a capacitance sensor and is suitably provided in a battery cell in accordance with the disclosure comprises two electrodes (charge carriers), and a gap, preferably an open air gap, is located between the said two electrodes. An electrical connection that is embodied by way of example as a connection cable is provided in each case to the two electrodes.

The capacitor of the capacitance sensor is connected to a current circuit of a current supply circuit in such a manner that one electrode is positively charged and the other electrode is negatively charged. The capacitance of the capacitor of the capacitance sensor is measured by way of the subsequent measuring circuit, said capacitance being greatly influenced by the dielectric value of the environment. The circuits for the current supply (current supply circuit) and/or for the measurement evaluating (measuring circuit) can be integrated into the existing hardware and software of the battery cell or added as additional components.

The capacitor of the capacitance sensor is provided in the battery cell in such a manner that the graphite particles that are entrained in a gas that is being discharged through an open excess pressure valve of the battery cell also deposit themselves in the air gap of the capacitor that is encompassed by the capacitance sensor. The dielectric value in the air gap changes as a consequence and consequently the measured capacitance of the capacitor changes. This change in capacitance is ascertained by way of the correspondingly embodied measuring circuit (measuring control) and, if the battery cell is arranged in a battery system, can be transmitted to the battery management system of the battery system. It is preferred that the battery management system identifies the battery cell that is defective and subsequently discharges said battery cell.

In the case of a very much preferred embodiment of the battery cell in accordance with the disclosure, the electrodes of the capacitor are embodied in an annular manner. It is preferred that the electrodes of the capacitor extend fully inside the battery cell housing. It is preferred that the capacitor of the battery cell in accordance with the disclosure is arranged on the battery cell cover. Thus, the electrodes of the capacitor can be arranged around or rather in a circular manner around the excess pressure valve that is provided on the battery cell cover, in particular on the upper face of the battery cell cover. It is further preferred that the capacitor is arranged in a gas discharge duct of the battery cell, said gas discharge duct being provided on the excess pressure valve.

Consequently, the capacitance sensor of a capacitor comprises two annular electrodes (charge carriers) that are preferably fully integrated in the electrically non-conductive housing of the battery cell. The suitably embodied capacitance sensor is preferably located around the excess pressure valve on the upper face of the battery cell cover. A capacitance sensor of this type can also be mounted at a different suitable site of the battery cell, such as for example in the gas discharge duct.

A further aspect of the disclosure relates to a battery system comprising a battery having a plurality of battery cells in accordance with the disclosure. The battery system in accordance with the disclosure comprises a battery management system and is embodied for the purpose by means of the battery management system of recognizing and identifying as defective any of the battery cells in accordance with the disclosure in the presence of a change in the capacitance of the capacitor. Moreover, the battery system in accordance with the disclosure is embodied for the purpose of discharging a battery cell that has been identified by means of the battery management system as being defective and in particular for bridging said defective battery cell.

A further aspect of the disclosure relates to a vehicle having a battery system in accordance with the disclosure comprising a battery having a plurality of battery cells in accordance with the disclosure.

BRIEF DESCRIPTION OF THE DRAWINGS

Exemplary embodiments of the disclosure are described in detail hereinunder with reference to the accompanying drawing, in which.

DETAILED DESCRIPTION

Figure 1:
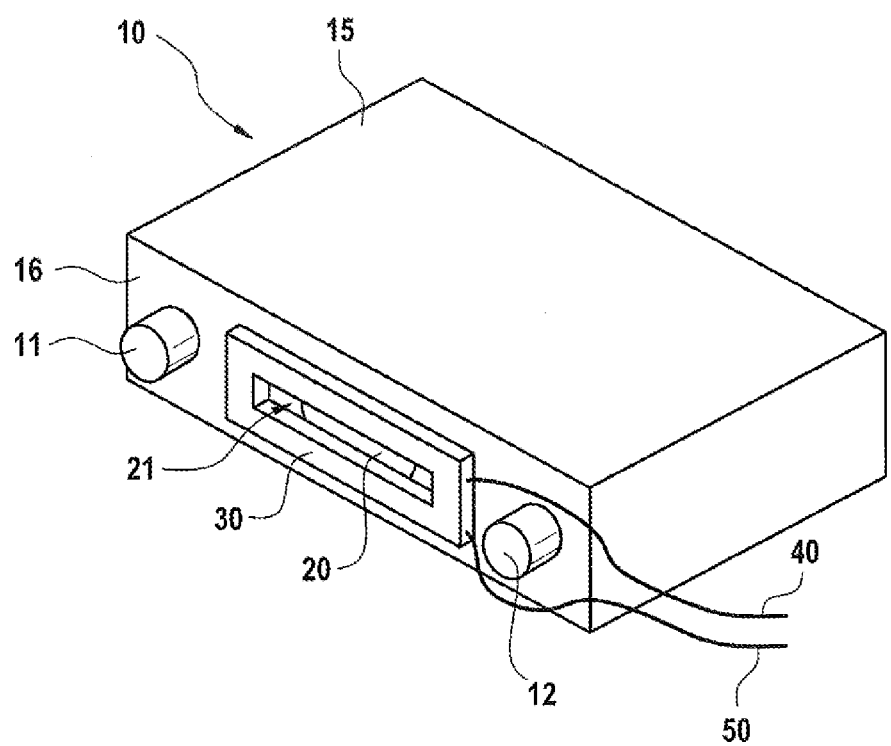
FIG. 1 illustrates a perspective view of a lithium ion battery cell according to a first embodiment of the disclosure, wherein the battery cell comprises an excess pressure valve and a capacitance sensor.

FIG. 1 illustrates a perspective view of a lithium ion battery cell 10 according to a first embodiment of the disclosure. The lithium ion battery cell 10 comprises a graphite cathode [not illustrated] and an excess pressure valve 20 that is mounted on the upper face of the battery cell cover 16 and is embodied for the purpose of opening in the presence of a predetermined battery cell internal pressure and discharging gas that has been produced inside the battery cell 10, said gas being discharged together with graphite particles that are entrained in the gas that is being discharged. The two battery cell terminals 11, 12 are also mounted on the battery cell cover 16. The battery cell housing 15 is designated by the reference numeral 15.

Moreover, the battery cell 10 comprises a capacitance sensor having a capacitor that is integrated in the excess pressure valve 20 on the upper face of the battery cell cover 16 and said capacitor extends around said battery cell cover. The capacitance sensor that is embodied corresponding to the excess pressure valve 20 encompasses a surface 21. Two connection cables 40, 50 are mounted on the capacitance sensor and are provided for the purpose of charging the capacitor that is provided in the capacitance sensor.

Figure 2:
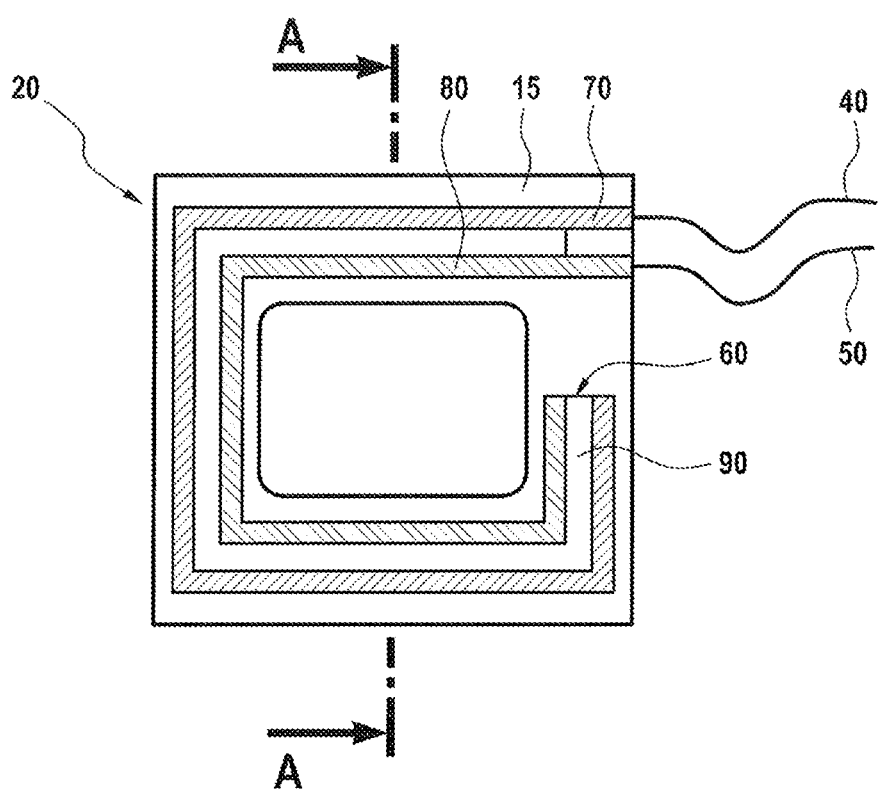
FIG. 2 illustrates a first sectional view of the capacitance sensor of the battery cell illustrated in FIG. 1.

FIG. 2 illustrates a first sectional view of the capacitance sensor of the battery cell 10 illustrated in FIG. 1, said capacitance sensor being integrated in the excess pressure valve 20. The section plane of the first sectional view extends in parallel to the surface 21 that is encompassed by the capacitance sensor. The capacitance sensor comprises a capacitor 60 having two electrodes 70, 80. One of the two electrodes 70 that is also described as the outer electrode 70 is mounted inside the battery cell 10 adjacent to the battery cell housing. The other of the two electrodes that is described as the inner electrode 80 is mounted inside the battery cell 10 spaced apart from the outer electrode 70. An open air gap 90 is provided between the two electrodes 70, 80. FIG. 2 also illustrates the two connection cables 40, 50 that are provided for charging the capacitor 60. The connection cable 40 is electrically connected to the outer electrode 70. The connection cable 50 is electrically connected to the inner electrode 80.

Figure 3:
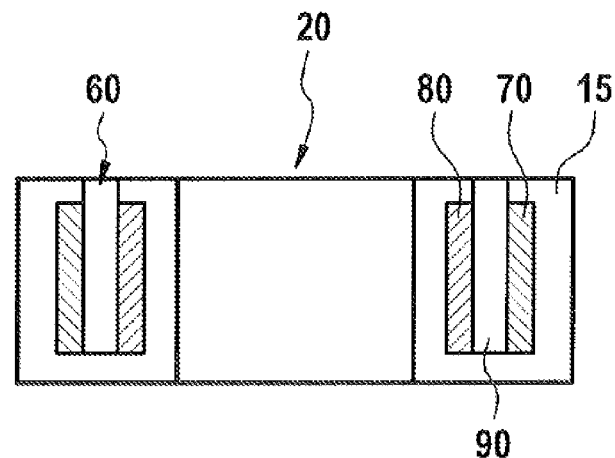
FIG. 3 illustrates a second sectional view of the capacitance sensor of the battery cell illustrated in FIG. 1 with the excess pressure valve closed.

FIG. 3 illustrates a second sectional view of the capacitance sensor of the battery cell 10 that is illustrated in FIG. 1. The section plane of the second sectional view is identified in FIG. 2 by the reference letters AA and extends perpendicular to the surface 21 that is encompassed by the capacitance sensor. FIG. 3 illustrates the capacitance sensor in a condition of the battery cell 10 that is illustrated in FIG. 1, wherein the excess pressure valve 20 is closed. FIG. 3 illustrates the capacitor 60 with its outer electrode 70 that is adjacent to the battery cell housing 15 and with its inner electrode 80 that is arranged spaced apart from the outer electrode 70. FIG. 3 also illustrates the open air gap 90 that is also located between the electrodes 70, 80.

Figure 4:
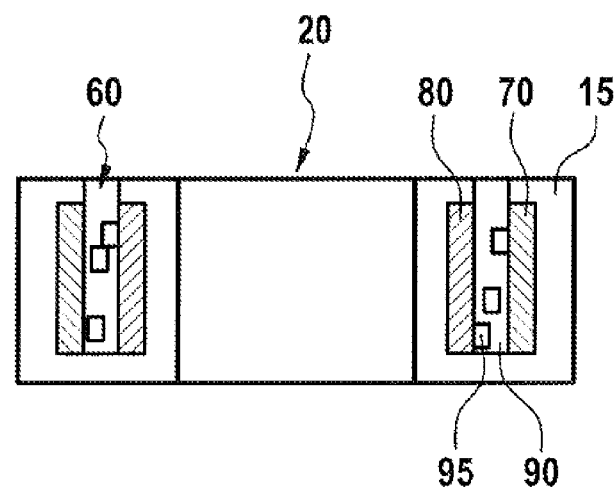
FIG. 4 illustrates a second sectional view of the capacitance sensor of the battery cell illustrated in FIG. 1 after gas has been discharged through the open excess pressure valve.

FIG. 4 likewise illustrates the second sectional view of the capacitance sensor of the battery cell 10 that is illustrated in FIG. 1, wherein the capacitance sensor is shown in a condition of the battery cell 10 that is illustrated in FIG. 1, wherein gas has already been discharged through the open excess pressure valve 20. Graphite particles 95 that are entrained in the gas that is being discharged are located here in the open air gap 90 between the two electrodes 70, 80 of the capacitor 60.

The capacitor 60 of the capacitance sensor is connected by way of the connection cable 40, 50 to a current circuit of a current supply circuit in such a manner that one of its electrodes 70, 80 is positively charged and the other of its electrodes 70, 80 is negatively charged. The capacitance of the capacitor 60 is measured by way of the subsequent measuring circuit. The current supply circuit and the measuring circuit can be integrated in each case as circuits for the current supply into the existing hardware and software of the battery cell 10 or can be added as additional components.

Graphite particles 95 are also entrained in the gas as said gas is discharged through the open excess pressure valve 20. Said graphite particles deposit themselves in the air gap 90 of the capacitor 60 of the capacitance sensor. The dielectric value in the air gap 90 of the capacitor 60 consequently changes and as a consequence the measured capacitance of the capacitor 60 changes. A defect of the battery cell 10 is established in the presence of a change of this type in capacitance.

In addition to the above written disclosure, reference is hereby made for the purpose of further disclosing the disclosure in addition to the illustration in FIGS. 1 to 4.

What is claimed is:

1. A lithium ion battery cell, comprising:
    a graphite cathode;
    an excess pressure valve configured to open in a presence of a predetermined battery cell internal pressure and discharging gasses produced inside the lithium ion battery cell, wherein graphite particles are entrained in the discharging gasses; and
    at least one capacitor that is positioned in the lithium ion battery cell and configured such that:
        the graphite particles are deposited at least in part in a gap located between two electrodes of the at last one capacitor; and
        the graphite particles being deposited at least in part in the gap causes change in a dielectric value of in the gap, wherein the change in the dielectric value causes a change in a capacitance of the at least one capacitor.

2. The lithium ion battery cell according to claim 1, further comprising:
    a communication site configured to communicate with a battery management system; and
    a measuring circuit configured to measure the capacitance of the at least one capacitor, ascertain a change in the capacitance, and provide information regarding an ascertained change in the capacitance via the communication site.

3. The lithium ion battery cell according to claim 1, further comprising a current supply circuit that is connected to or is configured to be connected to the two electrodes of the at least one capacitor, and is further configured to positively charge one of the two electrodes and negatively charge an other of the two electrodes.

4. The lithium ion battery cell according to claim 1, wherein the gap is at least one of an open gap and an air gap.

5. The lithium ion battery cell according to claim 1, wherein at least one of:
    the two electrodes of the at least one capacitor have a substantially annular shape;
    the two electrodes extend fully inside a housing of the lithium ion battery cell;
    the at least one capacitor is positioned on an upper face of a cover of the lithium ion battery cell, and the two electrodes are positioned in a circular manner around the excess pressure valve; and
    the at least one capacitor is positioned in a gas discharge duct situated on the excess pressure valve.

6. A method for monitoring a condition of a lithium ion battery cell that has a graphite cathode and an excess pressure valve, wherein graphite particles are entrained in discharging gasses produced inside the lithium ion battery cell, the method comprising:
    obtaining a measurement of a capacitance of at least one capacitor positioned in the lithium ion battery cell and configured such that the graphite particles are deposited at least in part in a gap located between two electrodes of the capacitor and cause a change in a dielectric value in the gap, wherein a change in the dielectric value causes a change in the capacitance;
    establishing a defective condition of the lithium ion battery cell in a presence of a change in the capacitance; and
    discharging defective condition gas out of the lithium ion battery cell through an open excess pressure valve, wherein the excess pressure valve is configured to open in a presence of a predetermined battery cell internal pressure and the discharging gasses.

7. The method according to claim 6, further comprising:
    ascertaining the change in the capacitance; and
    providing the ascertained change in the capacitance via a communication site positioned on the lithium ion battery cell and configured to communicate with a battery management system.

8. The method according to claim 6, wherein one of the two electrodes is positively charged and an other of the two electrodes is negatively charged via a current supply circuit that is positioned in the lithium ion battery cell and that is connected to the two electrodes.

9. A battery system comprising:
    a battery that includes a plurality of battery cells that respectively have:
        a graphite cathode;
        an excess pressure valve configured to open in a presence of a predetermined battery cell internal pressure and discharging gasses produced inside each battery cell, wherein graphite particles are entrained in the discharging gasses; and
        at least one capacitor that is positioned in each battery cell and configured such that:
            the graphite particles are deposited at least in part in a gap located between two electrodes of the at last one capacitor; and
            the graphite particles being deposited at least in part in the gap causes change in a dielectric value of in the gap, wherein the change in the dielectric value causes a change in a capacitance of the at least one capacitor; and
    a battery management system, wherein the battery system is configured to:
        recognize and identify, via the battery management system, any of the plurality of battery cells as being defective in a presence of a change in the capacitance of a respective battery cell; and
        discharge and bridge the respective battery cell that has been identified as defective.

10. The battery system according to claim 9, wherein the battery system is comprised by and configured to be used in a vehicle.

* * * * *

UNITED STATES PATENT AND TRADEMARK OFFICE
CERTIFICATE OF CORRECTION

| | | |
|---|---|---|
| PATENT NO. | : 9,276,297 B2 | |
| APPLICATION NO. | : 14/296556 | |
| DATED | : March 1, 2016 | |
| INVENTOR(S) | : Hald et al. | |

It is certified that error appears in the above-identified patent and that said Letters Patent is hereby corrected as shown below:

Claims

In column 5, lines 33-35, such portion of claim 1 should read:

> the graphite particles are deposited at least in part in a gap located between two electrodes of the at least one capacitor; and In column 6, lines 46-48, such portion of claim 9 should read:

> the graphite particles are deposited at least in part in a gap located between two electrodes of the at least one capacitor; and Signed and Sealed this
Twelfth Day of July, 2016

Michelle K. Lee
*Director of the United States Patent and Trademark Office*